United States Patent [19]

Gee et al.

[11] Patent Number: 5,103,654

[45] Date of Patent: Apr. 14, 1992

[54] TENSIOMETER WITH REMOVABLE WICK

[75] Inventors: Glendon W. Gee; Melvin D. Campbell, both of Richland, Wash.

[73] Assignee: Battelle Memorial Institute, Richland, Wash.

[21] Appl. No.: 596,813

[22] Filed: Oct. 11, 1990

[51] Int. Cl.[5] ............................................ G01N 19/10
[52] U.S. Cl. ............................................ 73/73; 73/38
[58] Field of Search ............................................ 73/38, 73

[56] References Cited

U.S. PATENT DOCUMENTS

| | | | |
|---|---|---|---|
| 2,878,671 | 3/1959 | Prosser et al. | 73/73 |
| 3,443,420 | 5/1969 | McMahan | 73/73 |
| 3,898,872 | 8/1975 | Skaling et al. | 73/73 |

FOREIGN PATENT DOCUMENTS 435815  10/1926  Fed. Rep. of Germany ......... 73/73

*Primary Examiner*—Hezron E. Williams
*Assistant Examiner*—Joseph W. Roskos
*Attorney, Agent, or Firm*—Paul W. Zimmerman

[57] ABSTRACT

The present invention relates to improvements in tensiometers for measuring soil water tension comprising a rod shaped wick. the rod shaped wick is shoestring, rolled paper towel, rolled glass microfiber filter, or solid ceramic. The rod shaped wick is secured to the tensiometer by a cone washer and a threaded fitting.

7 Claims, 2 Drawing Sheets

TENSIOMETER WITH REMOVABLE WICK

This invention was made with Government support under Contract DE-AC06-76RLO 1830 awarded by the U.S. Department of Energy. The Government has certain rights in the invention.

FIELD OF THE INVENTION

The present invention relates generally to a means for measuring soil water tension, or more specifically to improvements in means for measuring soil water tension comprising means for replacement of a wick.

BACKGROUND OF THE INVENTION

Measurement of soil water tension is useful in determining moisture content of soil, for example in farmland to determine irrigation scheduling. Instruments for measurements of soil water tension, or tensiometers, are described in Chapter 23 of "Methods of Soil Analysis" (D. K. Cassell and A. Klute 1986, American Society of Agronomy, Madison, Wis.) (ref) and generally comprise a sealed water reservoir, a solid wicking material mounted at the bottom of the reservoir in contact with the water within the reservoir and extending into the soil to be measured, and a means for measuring pressure within the reservoir. The measured pressure ranges from 0.0 to 700.0 cm water and may be measured with a manometer or with a hypodermic inserted through a septum mounted on the top of the tensiometer opposite the wick material. Commercially available tensiometers also known as ceramic cup tensiometers, have an inflexible ceramic cup as the wick. The ceramic cup is permanently bonded to the bottom of the water reservoir.

In operation, it is necessary to maintain an air tight seal against the vacuum that is created within the tensiometer water reservoir when water is drawn through the saturated wick into the unsaturated soil. It is also necessary that the water reservoir and wick resist large deflections that may be caused by the vacuum. The commercially available ceramic cup tensiometers meet these requirements by using a rigid porous ceramic material in the shape of a cup for the wick, and by permanently bonding the ceramic cup to the water reservoir.

SUMMARY OF THE INVENTION

The present invention comprises improvement to soil tensiometers wherein the improvement comprises a means for replacement of a wick, said means further comprising a rod shaped wick, and a threaded fitting together with a cone washer to hold and seal the perimeter of the rod shaped wick. The rod shaped wick may be a solid porous material such as ceramic or a flexible material such as shoelaces, paper toweling, or glass microfiber filter.

It will be appreciated by those skilled in the art that substitution of a permanently bonded non-replaceable ceramic cup with a replaceable wick has the advantages of reduced time and cost of field repairs and maintenance of tensiometers.

It will be further appreciated by those skilled in the art that a rod shaped wick, especially one made from a flexible material, is less susceptible to breaking during handling and when the tensiometer is inserted into rocky soil.

It will be further appreciated by those skilled in the art that a rod shaped wick, especially one made from a flexible material, has the advantage of reduced cost of the wick material.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
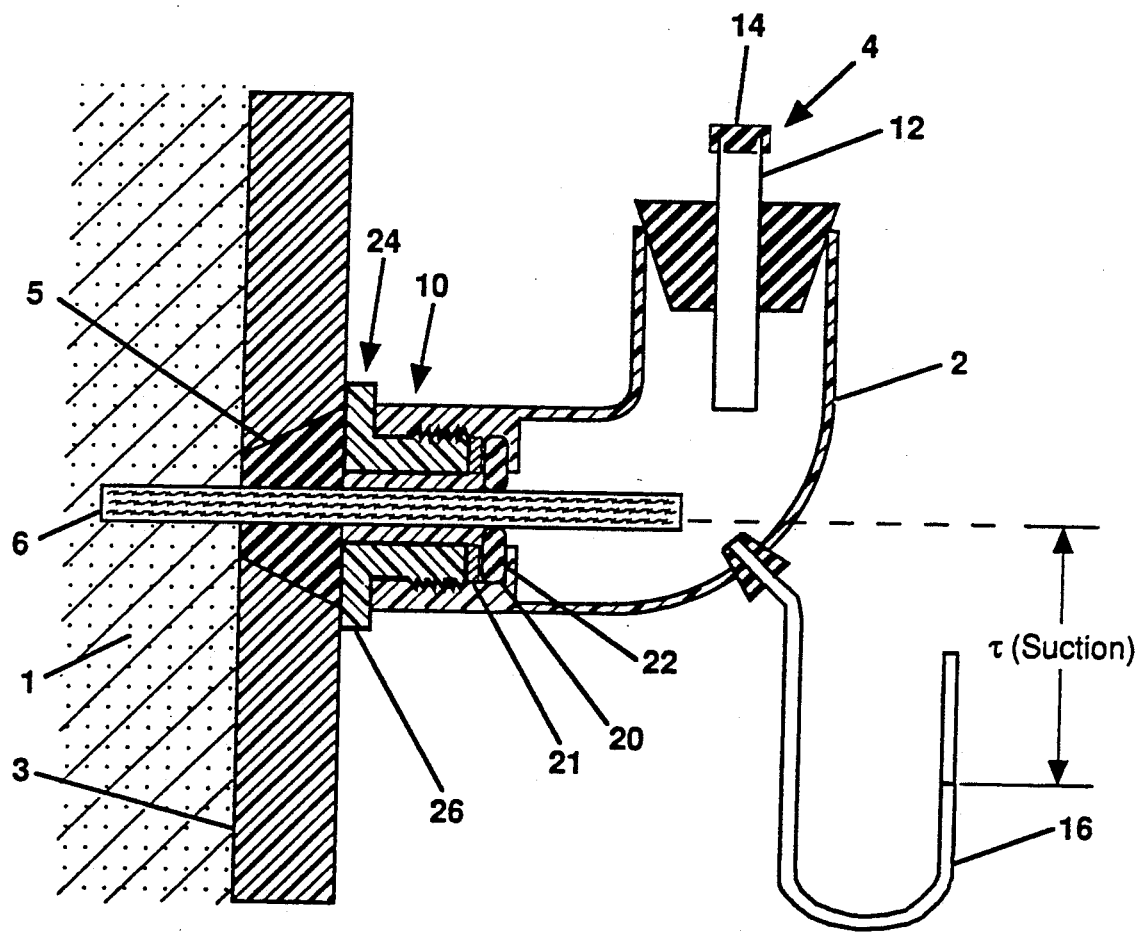
FIG. 1 is a cut-away view of an elbow shaped tensiometer.
Figure 2:
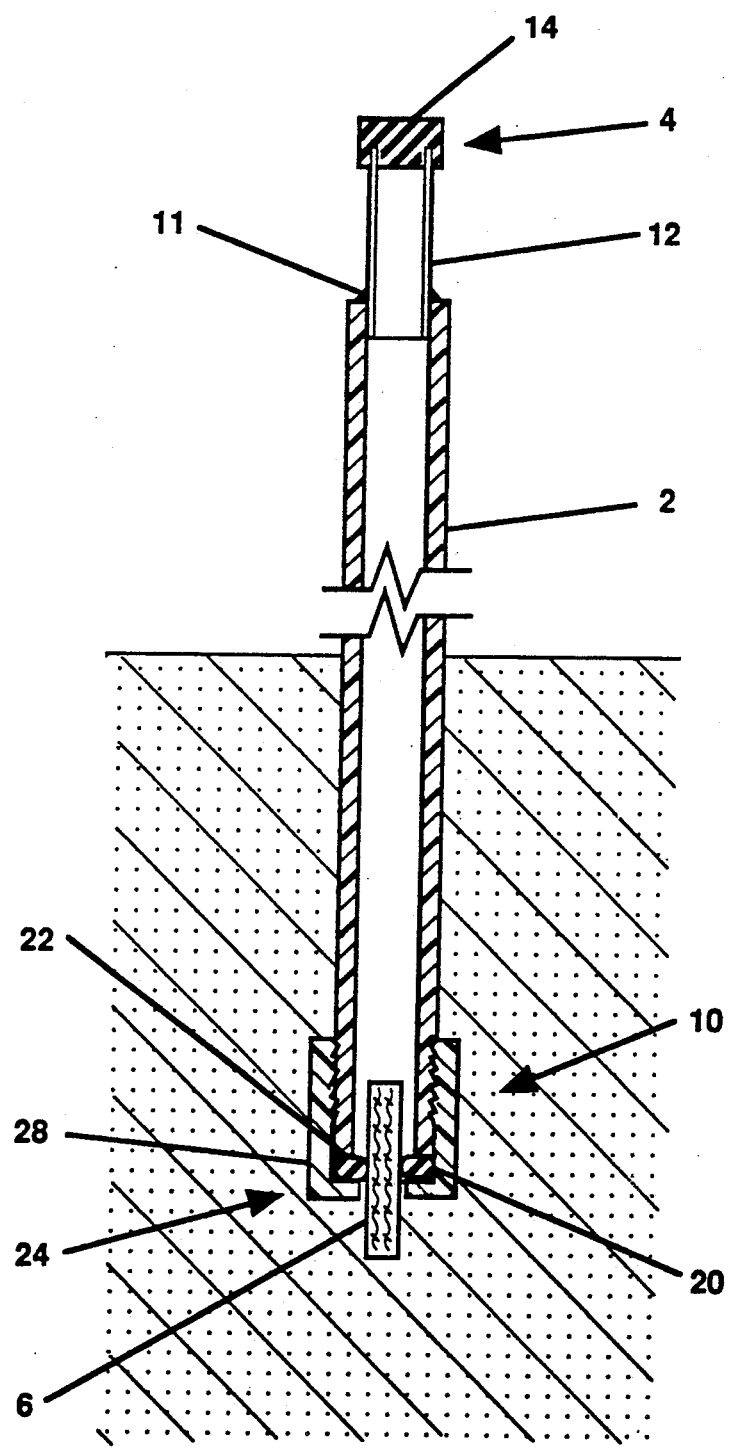
FIG. 2 is a cut-away view of a straight tensiometer.

Embodiments of improved tensiometers are shown in FIGS. 1 and 2.

The elbow shaped tensiometer of FIG. 1 is the preferred embodiment for laboratory applications wherein soil (1) is kept in containers (3) and access to the soil for tensiometer measurements is through ports (5) in the sides of the containers. The straight tensiometer of FIG. 2 is the preferred embodiment for field applications wherein the tensiometer is inserted into soil in a field or into soil in a container having access to the soil from the top.

Both embodiments comprise a water reservoir (2), means for measuring pressures (4), said pressures ranging from about 0.0 to about 100.0 cm or greater water, rod shaped wick (6) sealably inserted into the bottom of the water reservoir and extending from the water reservoir into soil, and means for replacement (10) of the rod shaped wick.

The water reservoir (2) may be made of plastic or metal pipe, tubing, or fittings. In the preferred embodiment, the water reservoir is made of plastic pipe, with a low air-diffusion rate.

Means for measuring pressure (4) comprises a clear sight tube (12) sealably inserted into the top of the water reservoir (2) and a septum (14) sealably attached to the top of the clear sight tube (12) through which a hypodermic needle may be inserted for determination of pressure. An alternative means for measuring pressure is a manometer tube (16) as shown in FIG. 1.

The rod shaped wick (6) must not deform under the vacuum. In the preferred embodiment, this is achieved either by rolling a sheet of flexible porous material into a tight spiral and having an approximately cylindrical rod external shape, or by use of an inflexible porous ceramic material having an approximately cylindrical rod external shape. The rod shaped wick (6) having a first end and a second end is inserted into the water reservoir (2) such that said first end extends into said water reservoir and is in contact with water, and said second end extends beyond the water reservoir into the soil. The rod shaped wick (6) is inserted into the water reservoir (2) such that the longitudinal axis of the rod shaped wick is perpendicular to the cross section of the bottom of the water reservoir. In this orientation, the rod shaped wick can resist deformation by a force exerted along its longitudinal axis by the vacuum.

Several materials were tested for use as a rod shaped wick including shoestrings, paper towels, and glass microfiber filters. The shoestrings were not rolled as previously described but showed good wicking ability.

However, response time was slow (on the order of days) for higher pressures. Shoestrings and similar materials may be useful in the 0.0 to 30.0 cm water pressure range. Paper towels showed good wicking ability and good response time (2–4 hours) in the low tension range. Several varieties were tested with no differences noted. However, long term use of paper towels (on the order of months) resulted in the formation of slime and subsequent reduction in wicking ability. Nevertheless, paper toweling is a preferred material in terms of its low cost and good performance over short time periods. Glass microfiber filters showed good wicking ability, good response time (2–4 hours), and resisted formation of slime over long periods.

The means for replacement (10) of the rod shaped wick (6) comprises a cone washer (20), a sealing surface (22) against which the cone washer is pressed, and a threaded fitting (24) which is threadably engaged with the water reservoir (2) and upon tightening presses the cone washer (20) against the sealing surface (22). Another washer (21) may be inserted between the threaded fitting (24) and the cone washer (20). The rod shaped wick (6) may engage an inner diameter of the port (5) as shown in FIG. 1, or there may be a circumferential gap between the inside diameter of the port (5) and the rod shaped wick (6).

The cone washer (20) is preferably rubber although any elastomeric material will suffice. The cone washer has a hole through which the rod shaped wick (6) extends. A vacuum tight seal is formed between the flexible water absorbing wick and the cone washer.

The sealing surface (22) may be a surface machined into the interior of the water reservoir (2) as shown in FIG. 1, or simply the end of the water reservoir as shown in FIG. 2.

The threaded fitting (24) may be male as the male fitting (26) (FIG. 1) or female as the female fitting (28) (FIG. 2) on either of the elbow shaped tensiometer or the straight tensiometer.

Other combinations of sealing surface and thread type such as bolted connections, quick release quarter turn or lever connectors may be preferred in particular applications.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A tensiometer including the elements water reservoir, pressure measuring means for measuring pressure within said reservoir, and a wick having a first end and a second end, said first end extending into said water reservoir, and said second end extending beyond the water reservoir into soil, wherein the improvement comprises:
   said wick comprising a rod shaped wick.

2. A tensiometer as recited in claim 1, further comprising:
   a sealing surface near the bottom of said water reservoir,
   a fitting threadably engaged near the bottom of said water reservoir, and
   a cone washer having a hole through which said rod shaped wick extends, said cone washer being set between said sealing surface and said fitting, forming a seal with said rod shaped wick and said sealing surface and said fitting is tightened pressing said cone washer against said sealing surface and said rod shaped wick.

3. A tensiometer as in claim 1, wherein said rod shaped wick is solid porous material.

4. A tensiometer as in claim 3, wherein said solid porous material is flexible.

5. A tensiometer as in claim 1, wherein said rod shaped wick is, shoestring, rolled paper towel, or rolled glass microfiber filter.

6. A tensiometer including the elements water reservoir, pressure measuring means for measuring pressure within said reservoir, and a wick having a first and second end, said first end extending into said water reservoir, and said second end extending beyond the water reservoir into soil, wherein the improvement comprises:
   said wick comprising flexible porous material.

7. A tensiometer as recited in claim 6, further comprising:
   a sealing surface near the bottom of said water reservoir,
   a fitting threadably engaged near the bottom of said water reservoir, and
   a cone washer having a hole through which said wick extends, said cone washer being set between said sealing surface and said fitting, forming a seal with said wick and said sealing surface and said fitting is tightened pressing said cone washer against said sealing surface and said wick.

* * * * *